(12) United States Patent
Ng

(10) Patent No.: US 11,751,941 B2
(45) Date of Patent: *Sep. 12, 2023

(54) APPARATUS AND METHOD OF ASSESSING TRANSVASCULAR DENERVATION

(71) Applicant: St. Jude Medical, Inc., St. Paul, MN (US)

(72) Inventor: Kok-Hwee Ng, Irvine, CA (US)

(73) Assignee: St. Jude Medical, Inc., St. Paul, MN (US)

( * ) Notice: Subject to any disclaimer, the term of this patent is extended or adjusted under 35 U.S.C. 154(b) by 18 days.

This patent is subject to a terminal disclaimer.

(21) Appl. No.: 17/574,122

(22) Filed: Jan. 12, 2022

(65) Prior Publication Data

US 2022/0133404 A1 May 5, 2022

Related U.S. Application Data

(63) Continuation of application No. 16/018,577, filed on Jun. 26, 2018, now Pat. No. 11,241,280, which is a
(Continued)

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/0215* (2013.01); *A61B 5/6853* (2013.01);
(Continued)

(58) Field of Classification Search
None
See application file for complete search history.

(56) References Cited

U.S. PATENT DOCUMENTS

| 3,650,277 A | 3/1972 | Sjostrand et al. |
| 4,519,403 A | 5/1985 | Dickhudt |

(Continued)

FOREIGN PATENT DOCUMENTS

| WO | 9745157 A1 | 12/1997 |
| WO | 0066020 A1 | 11/2000 |

(Continued)

OTHER PUBLICATIONS

Kirchheim, H. et al, Sympathetic Modulation of Renal Hemodynamics, Renin Release and Sodium Excretion, Klin VVochenschr (1989) 67: 858-864.

(Continued)

*Primary Examiner* — Carrie R Dorna
(74) *Attorney, Agent, or Firm* — Armstrong Teasdale LLP

(57) ABSTRACT

A catheter apparatus for assessing denervation comprises: an elongated catheter body; a deployable structure coupled to the catheter body, the deployable structure being deployable outwardly from and contractible inwardly toward the longitudinal axis of the catheter body; one or more ablation elements disposed on the deployable structure to move outwardly and inwardly with the deployable structure; one or more stimulation elements spaced from each other and disposed on the deployable structure to move with the deployable structure, the stimulation elements being powered to supply nerve stimulating signals to the vessel; and one or more recording elements spaced from each other and from the stimulation elements, the recording elements being disposed on the deployable structure to move with the deployable structure, the recording elements configured to record response of the vessel to the nerve stimulating signals.

16 Claims, 9 Drawing Sheets

Related U.S. Application Data continuation of application No. 14/537,109, filed on Nov. 10, 2014, now Pat. No. 10,179,026, which is a continuation of application No. 13/153,838, filed on Jun. 6, 2011, now Pat. No. 8,909,316, which is a continuation-in-part of application No. 13/110,041, filed on May 18, 2011, now abandoned.

(51) Int. Cl.
  *A61B 18/00* (2006.01)
  *A61B 5/0215* (2006.01)
  *A61B 90/00* (2016.01)
  *A61B 5/24* (2021.01)

(52) U.S. Cl.
  CPC .............. *A61B 5/24* (2021.01); *A61B 5/6885* (2013.01); *A61B 2018/0016* (2013.01); *A61B 2018/0022* (2013.01); *A61B 2018/00226* (2013.01); *A61B 2018/00267* (2013.01); *A61B 2018/00345* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00672* (2013.01); *A61B 2018/00678* (2013.01); *A61B 2018/00702* (2013.01); *A61B 2018/00839* (2013.01); *A61B 2018/1475* (2013.01); *A61B 2090/064* (2016.02)

(56) References Cited

U.S. PATENT DOCUMENTS

| | | |
|---|---|---|
| 4,658,819 A | 4/1987 | Harris et al. |
| 4,976,711 A | 12/1990 | Parins et al. |
| 5,035,694 A | 7/1991 | Kasprzyk et al. |
| 5,117,828 A | 6/1992 | Metzger et al. |
| 5,142,558 A * | 8/1992 | Franciose ............... A61B 6/504 378/98.2 |
| 5,255,679 A | 10/1993 | Imran |
| 5,300,068 A | 4/1994 | Rosar et al. |
| 5,312,339 A | 5/1994 | Boussignac et al. |
| 5,342,303 A | 8/1994 | Ghaerzadeh |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl |
| 5,598,848 A | 2/1997 | Swanson et al. |
| 5,603,333 A | 2/1997 | Konings |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,836,874 A | 11/1998 | Swanson et al. |
| 5,846,238 A | 12/1998 | Jackson et al. |
| 5,860,974 A | 1/1999 | Abele |
| 5,891,027 A | 4/1999 | Tu et al. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 5,985,307 A | 11/1999 | Hanson et al. |
| 5,997,571 A | 12/1999 | Farr et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,091,993 A | 7/2000 | Bouchier et al. |
| 6,096,037 A | 8/2000 | Mulier et al. |
| 6,117,101 A | 9/2000 | Diederich et al. |
| 6,123,718 A | 9/2000 | Tu et al. |
| 6,139,545 A | 10/2000 | Utley et al. |
| 6,142,993 A | 11/2000 | Whayne et al. |
| 6,161,543 A | 12/2000 | Cox et al. |
| 6,178,349 B1 | 1/2001 | Kieval |
| 6,192,275 B1 | 2/2001 | Zhu et al. |
| 6,200,312 B1 | 3/2001 | Zikorus et al. |
| 6,216,044 B1 | 4/2001 | Kordis |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hegde et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,150,745 B2 | 12/2006 | Stern et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,499,748 B2 | 3/2009 | Moffitt et al. |
| 7,632,268 B2 | 12/2009 | Utley et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,749,220 B2 | 7/2010 | Schmaltz |
| 7,850,685 B2 | 12/2010 | Christopher et al. |
| 7,949,407 B2 | 5/2011 | Kaplan et al. |
| 8,140,170 B2 | 3/2012 | Rezai et al. |
| 8,145,316 B2 | 3/2012 | Deem et al. |
| 8,224,416 B2 | 7/2012 | De La Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,473,067 B2 | 6/2013 | Hastings et al. |
| 8,545,495 B2 | 10/2013 | Scheib |
| 9,022,948 B2 | 5/2015 | Wang |
| 2002/0068885 A1 | 6/2002 | Paul et al. |
| 2002/0120304 A1 | 8/2002 | Mest |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2003/0236455 A1 | 12/2003 | Swanson et al. |
| 2004/0215186 A1 | 10/2004 | Cornelius et al. |
| 2005/0096647 A1 | 5/2005 | Steinke et al. |
| 2005/0288730 A1 | 12/2005 | Deem et al. |
| 2006/0089678 A1 | 4/2006 | Shalev |
| 2007/0060921 A1 | 3/2007 | Janssen et al. |
| 2007/0135875 A1 | 6/2007 | Demarais et al. |
| 2008/0249464 A1 | 10/2008 | Spencer et al. |
| 2008/0255478 A1 | 10/2008 | Burdette |
| 2009/0024195 A1 | 1/2009 | Rezai et al. |
| 2009/0076409 A1 | 3/2009 | Wu et al. |
| 2010/0016762 A1 | 1/2010 | Thapliyal et al. |
| 2010/0076426 A1 | 3/2010 | De La Rama et al. |
| 2010/0087782 A1 | 4/2010 | Ghaffari et al. |
| 2010/0094209 A1 | 4/2010 | Drasler et al. |
| 2010/0113939 A1 | 5/2010 | Mashimo et al. |

(56) References Cited

U.S. PATENT DOCUMENTS

| | | |
|---|---|---|
| 2010/0168737 A1 | 7/2010 | Grunewald |
| 2010/0222851 A1 | 9/2010 | Deem et al. |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2010/0317921 A1 | 12/2010 | Marple et al. |
| 2011/0004087 A1 | 1/2011 | Fish et al. |
| 2011/0040232 A1 | 2/2011 | Magal |
| 2011/0118726 A1 | 5/2011 | De La Rama et al. |
| 2011/0137298 A1 | 6/2011 | Nguyen et al. |
| 2011/0160720 A1 | 6/2011 | Johnson et al. |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2011/0307034 A1 | 12/2011 | Hastings et al. |
| 2012/0143097 A1 | 6/2012 | Pike, Jr. |
| 2012/0143298 A1 | 6/2012 | Just et al. |
| 2012/0265198 A1 | 10/2012 | Crow et al. |
| 2012/0296232 A1 | 11/2012 | Ng |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| WO | 0100273 A1 | 1/2001 |
| WO | 0122897 A1 | 4/2001 |
| WO | 0226314 A1 | 4/2002 |
| WO | 02058785 A1 | 8/2002 |
| WO | 03082080 A2 | 10/2003 |
| WO | 2006041881 A2 | 4/2006 |
| WO | 2007149970 A2 | 12/2007 |
| WO | 2008092246 A1 | 8/2008 |
| WO | 2008141150 A2 | 11/2008 |
| WO | 2008151001 A2 | 12/2008 |
| WO | 2012064818 A1 | 5/2012 |
| WO | 2012106492 A1 | 8/2012 |

OTHER PUBLICATIONS

Klein, GE et al, Endovascular Treatment of Renal Artery Aneurysms with Conventional Non-Detachable Microcoils and Guglielmi Detachable Coils, Br J Urol. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanovvska-Jezierska, Elzbieta et al, Early Effects of Renal Denervation in the Anaesthetised Rat Matriuresis and Increased Cortical Blood Flow, Journal of Physiology (2001), 531.2, pp. 527-534.

Kreulen, D. "Activation of Mesenteric Arteries and Veins by Preganglionic and Postganglionic Nerves", American Physiological Society, 1986, pp. H1267-H1275.

Krum, Henry et al, Catheter-Based Renal Sympathetic Denervation for Resistant Hypertension: A Multicentre Safety and Proof-of-Principle Cohort Study, www.thelancel.com vol. 373 Apr. 11, 2009 1275-1281.

Krum, Henry et al, Device-Based Antihypertensive Therapy: Therapeutic Modulation of the Autonomic Nervous System, Circulation. 2011;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.

Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.

Labonte, Sylvain, Numerical Model for Radio-Frequency Ablation of the Endocardium and its Experimental Validation, IEEE Transactions on Biomedical Engineering, vol. 41, No. Feb. 2, 1994, 108-115.

Ambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luff, S.E. Ultrastructure of Sympathetic Axons and Their Structural Relationship with Vascular Smooth Muscle, Anatomy Embryology, 1995, vol. 193, pp. 515-531.

Luscher, Thomas F. et al, Renal Nerve Ablation After Symplicity HTN-3: Confused at the Higher Level? European Heart Journal, doi:10.1093/eurheartj/ehu195; May 14, 2014.

Lustgarten, Daniel L. et al, Cryothermal Ablation: Mechanism of Tissue Injury and Current Experience n the Treatment of Tachyarrhythmias, Progress in Cardiovascular Diseases, vol. 41, No. 6 (May/Jun.), 1999: pp. 481-498.

Mahfoud, Felix et al, Expert Consensus Document from the European Society of Cardiology on Catheter-Based Renal Denervation, European Heart Journal, Jul. 2013;34(28):2149-57.

Makita, Y., "Effects of Adrenoceptor Agonists and Antagonists on Smooth Muscle Cells and Neuromuscular Transmission in the Guinea-Pig Renal Artery and Vein", British Journal of Pharmacology, 1983, vol. 80, pp. 671-679.

Mancia, Giuseppe et al, Sympathetic Activation in the Pathogenesis of Hypertension and Progression of Organ Damage, Hypertension Journal of The American Heart Association, 1999, 34:724-728.

McGahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreel.com.

Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RON Therapy with the Symplicity Renal Denervation System, Procedure Fact Sheet, www.medtronic.com, 2011.

Medtronic, Inc., Renal Denervation (RON) Novel Catheter-based Treatment for Hypertension, Symplicity RON System Common Q&A, 2011.

Medtronic, Inc., Scientific Basis Behind Renal Denervation for the Control of Hypertension, Dec. 2012, http://www.icimeeting.com/2012/images/stories/PD F/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part 11, 316-321.

Mekata, F. "Different Electrical Responses of Outer and Inner Muscle of Rabbit Carotid Artery to Noradrenaline and Nerves", Journal of Physiology, 1984, vol. 346, pp. 589-598.

(56) References Cited

OTHER PUBLICATIONS

Mekata, F. "The Role of Hyperpolarization in the Relaxation of Smooth Muscle of Monkey Coronary Artery", Journal of Physiology, 1986, vol. 371, pp. 257-265.
Mekata, F., "Electrical Responses of Coronary Artery Smooth Muscle Associated with the Cardiac Muscle Action Potential in the Monkey", Journal of Physiology, 1991, vol. 439, pp. 239-256.
Meredith, I T et al, Exercise Training Lowers Resting Renal But Not Cardiac Sympathetic Activity in Humans Hypertension Journal of The American Heart Association, 1991;18:575-582.
Michaelis, Lawrence L. et al, Effects of Renal Denervation and Renin Depletion on the Renal Responses to ntravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 4, 2000, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation Aug. 4, 1998;98(5):458-465.
Nam, T.S. et al, "Mechanism of Transmission and Modulation of Renal Pain in Cats; Effects of Transcutaneous Electrical Nerve Stimulation on Renal Pain", Yonsei Medical Journal, 1995, vol. 36, No. 2, pp. 187-201.
Nanni, Gregg S. et al, Control of Hypertension by Ethanol Renal Ablation, Radiology 148: 51-54, Jul. 1983.
Abboud, Francois M., The Sympathetic System in Hypertension, State-of-the-Art Review, Hypertension Journal of the American Heart Association, Hypertension 4 (suppl II): 11-208-11-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Anderson, W.P. et al, "Mechanisms Involved in the Renal Responses to Intraven, Housand Renal Artery Infusions of Noradrenaline in Conscious Dogs", Journal of Physiology, 1981, vol. 321, pp. 21-30.

Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Astrand, P. et al, "On the Secretory Activity of Single Varicosities in the Sympathetic Nerves Innervating the Rat Tail Artery", Journal of Physiology, 1989, vol. 409, pp. 207-220.
Astrand, P. et al, "Time Course of Transmitter Action at the Sympathetic Neuroeffector Junction in Rodent Vascular and Non-Vascular Smooth Muscle", Journal of Physiology, 1988, vol. 401, pp. 657-670.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical nvestigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Bevan, Ja et al, "Sympathetic Mechanisms in Blood Vessels: Nerve and Muscle Relationships", Annual Review of Pharmacology, 1973, vol. 13, pp. 269-285.
Bevan, Ja et al, "Sympathetic Nerve-Free Vascular Muscle", The Journal of Pharmacology and Experimental Therapeutics, 1967, vol. 157, pp. 117-124.
Bevan, Ja, "Some Characteristics of the Isolated Sympathetic Nerve-Pulmonary Artery Preparation of the Rabbit", Journal of Pharmacology and Experimental Therapeutics, 1962, vol. 137, pp. 213-218.
Bevan, Ja. "Some Bases of Differences in Vascular Response to Sympathetic Activity—Variations on a Theme", Circulation Research, 1979, vol. 45, No. 2, pp. 161-171.
Blankestijn, Peter J. et al, Renal Denervation: Potential Impact on Hypertension in Kidney Disease?, Nephrol Dial Transplant (2011) O: 1-3.
Blankestijn, Peter J. et al, Sympathetic Overactivity in Renal Failure Controlled by ACE Inhibition: Clinical Significance, Nephrol Dial Transplant, 2000, 15, 755-758.

(56) References Cited

OTHER PUBLICATIONS

Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Bolton, T.B. et al, "Are Junction Potentials Essential? Dual Mechanism of Smooth Muscle Cell Activation by 1 Transmitter Released from Autonomic Nerves", Quarterly Journal of Experimental Physiology, 1986, D vol. 71, pp. 1-28, Great Britain.
Brinkmann, Julia et al, Catheter-Based Renal Nerve Ablation and Centrally Generated Sympathetic Activity in Difficult-to-Control Hypertensive Patients Prospective Case Series, Hypertension 2012;60:1485-1490.
Brock, J.A et al, "Electrical Activity at the Sympathetic Neuroeffector Junction in the Guinea-Pig Vas Deferens", Journal of Physiology, vol. 399, 1988, pp. 607-632.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC Cardiovascular Interventions, vol. 6, No. 1, 2013, 1-9.
Burnstock, G. "Autonomic Neurotransmission: 60 Years Since Sir Henry Dale", Annual Review of Pharmacology & Toxicology, 2009, vol. 49, pp. 1-30.
Burnstock, G. "Physiology and Pathophysiology of Purinergic Neurotransmission", Physiology Review, Apr. 2007, vol. 87, pp. 659-797.
Burnstock, G., "Neurotransmitters and Trophic Factors in the Autonomic Nervous System", 1981, vol. 313, pp. 1-35.
Burnstock, G., "Non-synaptic Transmission at Autonomic Neuroeffector Junctions", Neurochemistry International, 2008, vol. 52, pp. 14-25.
Burnstock, G.. "Dual Control of Vascular Tone and Remodelling by ATP Released from Nerves and Endothelial Dells", Pharmocological Reports, vol. 60, 2008, pp. 12-20.
Calleary, Hickey D. et al, Pre-Transplant Bilateral Native Nephrectomy for Medically Refractory Hypertension, The Irish Medical Journal, Jul. -Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9:741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Chau, D. et al, "Ongoing and Stimulus-Evoked Activity of Sympathetically Correlated Neurons in the Intermediate tone and Dorsal Horn of Acutely Spinalized Rats", Journal of Americal Physiological Society, 2000, pp. 2699-2706.
Cho, S. et al, "Design of Electrode Array for Impedance Measurement of Lesions in Arteries", Institute of Physics Publishing—Physiological Measurement, 2005, vol. 26, pp. S19-S26.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11 ):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Steedman, WA "Micro-Electrode Studies on Mammalian Vascular Muscle", Journal of Physiology, 1966, vol. 186, pp. 382-400.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part 11, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Feigen, Corey L. et al., Segmental Renal Artery Embolization for Treatment of Pediatric Renovascular Hypertension, Journal of Vascular and Interventional Radiology, 1992; 3:111-117.
Teixeira, Maria Do Carmo et al, 1992; Role of the Peripheral Renin Profile in Predicting Blood Pressure Control After Bilateral Nephrectomy in Renal-Transplanted Patients, Nephrol Dial Transplant (1998) 13: 2092-2097.

(56) References Cited

OTHER PUBLICATIONS

Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Reporton Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition. Hypertension Journal of The American Heart Association, 1993;22:839-846.
Uchida, Fumiya et al, Effect of Radiofrequency Catheter Ablation on Parasympathetic Denervation: A Comparison ofThree Different Ablation Sites, PACE, vol. 21, Nov. 1998, Part 11, 2517-2521.
Valente, John F. et al, Laparoscopic Renal Denervation for Intractable ADPKD-Relaled Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 PI 2):R1599-R1604.
Von End, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.-Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66, Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al., Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Zazgornik, Jan et al, Bilateral Nephrectomy: The Best, but Often Overiooked, Treatment for Refractory Hypertension in Hemodialysis Patients, AJH 1998; 11:1364-1370.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.

Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Harder, D. et al, "Electrical Stimulation of the Endothelial Surface of Pressurized Cat Middle Cerebral Artery Results In TIX-Sensitive Vasoconstriction", Circulation Research, vol. 60, No. 6, Jun. 1987, pp. 831-836.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 PI 2):F738-F745.
Hoobler, S.W. et al., The Effects of Splanchnicectomy on the Blood Pressure in Hypertension, Circulation Journal of The American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Tlrial, J Am Soc Hypertens. Jul.-Aug. 2012;6(4):270-6.
Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, (2013) O: 1-8.
Huang, Shoei K. Stephen et al., Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-lnduced Hypertension in Rats, Hypertension Journal of The American Heart Association, 1998;32:249-254.
Humpreys, Michael H., Renal Nerves and CKD: Is Renal Denervation the Answer?, Journal of The American Socity of Nephrology, 2012, 23: 1-3.
International Search Report and Written Opinion for Application No. PCT/US2010/054637 dated Jan. 3, 2011.
International Search Report and Written Opinion for Application No. PCT/US2010/054684 dated Jan. 10, 2011.
Irigoyen, M.C.C. et al, Baroreftex Control of Sympathetic Activity in Experimental Hypertension, Brazilian Journal of Medical and Biological Research, (1998) 31: 1213-1220.
Izzo, Jr, Joseph L. et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal

(56) References Cited

OTHER PUBLICATIONS and Left Posterior Accessory AV Pathways (Chapter 16), 2002, Futura Publishing Company, Inc., 321-343.
Jaff, Michael R. et al, Kidney Stenting Lowers Blood Pressure in Patients with Severe Hypertension Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Dbesity, Hypertension vol. 25, No. 4, Part Apr. 2, 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al., Recurrence of Left Atrium-Pulmonary Vein Conduction Following Successful Disconnection in Asymptomatic Patients, Europace (2004) 6, 425e432.
Keatinge, W.R. "Blood-Vessels", British Medical Bulletin, 1979, vol. 35, No. 3, pp. 249-254.
Keatinge, W.R., "Electrical and Mechanical Response of Arteries to Stimulation of Sympathetic Nerves", Journal of Physiology, vol. 185, 1966, pp. 701-715.
Keef, K.D. et al, "Comparison of Neurotransmission with Nerve Trunk and Transmural Field Stimulation in Guinea-Pig Mesenteric Artery", Journal of Physiology, 1991, vol. 441, pp. 367-383.
Keef, K.D. et al, "Electrical Responses of Guinea Pig Coronary Artery to Transmural Stimulation", Circulation Research, Mar. 1988, vol. 62, pp. 585-595.
Killip 111, Thomas, Oscillation of Blood Flow and Vascular Resistance During Mayer Waves, Circulation Research, vol. XI, Dec. 1962, 987-993.

Kim, D.H. et al, "Materials for Multifunctional Balloon Catheters with Capabilities in Cardiac Electrophysiological Mapping and Ablation Therapy", Nature Materials, 2011, pp. 1-8.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Christ, G.J. et al, "Gap Junctions in Vascular Tissues- Evaluating the Role of Intercellular Communication in the Modulation of Vasomotor Tone", Circulation Research, 1996, vol. 79, pp. 631-646.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Cowen, T., "An Ultrastructural Comparison of Neuromuscular Relationships in Blood Vessels with Functional and Non-functional' neuromuscular Transmission", Journal of Neurocytology, vol. 13, 1984, pp. 369-392.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise US, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review-Part 11, Journal of the National Medical Association, May 1948, vol. 40, No. 3., 113-116.
Dailey, U.G., Surgical Treatment of Hypertension: A Review-Part 111, Journal of the National Medical Association, Jul. 1948, vol. 40, No. 4, 160-162.
Dailey, U.G., The Surgical Treatment Of Hypertension: A Review, Journal of the National Medical Association, Mar. 1948, vol. 40, No. 2, 76-79.
Davis, M.J. et al, "Signaling Mechanisms Underlying the Vascular Myogenic Response", Physiological Reviews, 1999, vol. 7 9, No. 2, pp. 387-423.
Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.
Decktor, D.L. et al., "A Study of Renal-Efferent Neurones and Their Neural Connexions within Cat Renal Ganglia Using Intracellular Electrodes", Journal Physiol, 1981, vol. 321, pp. 611-626, Great Britain.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, America Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part 11, 621-624.
Dibona, Gerald F., Renal Innervation and Denervation: Lessons from Renal Transplantation Reconsidered, Artificial Organs, vol. 11, No. 6, 1987, 457-462.

(56) References Cited

OTHER PUBLICATIONS

Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Dunn, W.R. et al, "Electrochemical and Electrophysiological Characterizations of Neurotransmitter Release from Sympathetic Nerves Supplying Rat Mesenteric Arteries", British Journal of Pharmacology, 1999, vol. 128, pp. 174-180.
Eckert, R.E. et al, "Regulation of Renal Artery Smooth Muscle Tone by a1-adrenoceptors: Role of Voltage-gated Calcium Channels and Intracellular Calcium Stores", Urol Res, 2000, vol. 28, pp. 122-127.
Elmula, Fadl et al, Renal Sympathetic Denervation in Patients With Treatment-Resistant Hypertension After Witnessed Intake of Medication Before Qualifying Ambulatory Blood Pressure, Hypertension 2013;62:526-532.
Emerson, G.G. et al, "Electrical Activation of Endothelium Evokes Vasodilation and Hyperpolarization along Hamster Feed Arteries", American Journal Physiology Hear Circ Physiol, 2001, vol. 280, pp. H160-H167.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Gourine, A.V. et al, "Purinergic Signalling in Autonomic Control", Trends in Neuroscience, 2009, vol. 32, No. 5, pp. 241-248.
Graham, J.M. et al, "Differences in Sensitivity to Vasoconstrictor Drugs within the Wall of the Sheep Carotid Artery", Jounral of Physiology, 1972, vol. 221, pp. 477-492.

Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Dbesity, and Congestive Heart Failure, Hypertension. 1998;31:64 67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the freatment of Hypertension, Annals of Surgery, Oct. 1941, vol. 114, No. 4, 753-775.
Ndegwa, S., Catheter-Based Renal Denervation for Treatment-Resistant Hypertension [Issues in emerging health technologies issue 121] Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al., Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oishi, H. et al, "Role of Membrane Potential in Vasomotion of Isolated Pressurized Rat Arteries", Life Sciences, 2002, vol. 71, pp. 2239-2248.
Oliveira, Vera LL et al, Renal Denervation Normalizes Pressure and Baroreceptor Reflex in High Renin Hypertension in Conscious Rats, Hypertension vol. 19, No. 2, Feb. 1992, Supplement 11, 11-17-11-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5 , pp. 253-255.
Oral, Hakan et al, Pulmonary Vein Isolation for Paroxysmal and Persistent Atrial Fibrillation, Circulation Journal of The American Heart Association, 2002; 105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreftex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.

(56) References Cited

OTHER PUBLICATIONS

Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, Jan. 10-15, 2002.
Pearce, John A. et al, Blood Vessel Architectural Features and Their Effect on Thermal Phenomena, Critical Reviews, vol. CR75, 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3):139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al., Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al., Blood Pressure Outcome of Angioplasty in Atherosclerotic Renal Artery Stenosis A Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System An Overview of Structure and Function, Journal of Pharmacological and Toxicological Methods 44 (2000) 333-340.
Putney, John Paul, Are Secondary Considerations Still "Secondary"? :An Examination of Objective Indicia of Monobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4:1886-1891, 2009.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation A Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Rummery, N.M. et al, "ATP is the Predominant Sympathetic Neurotransmitter in Rat Mesenteric Arteries at High Pressure", Journal of Physiology, vol. 582.2, 2007, pp. 745-754.
Sanderson, John E. et al., Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4):94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.

\* cited by examiner

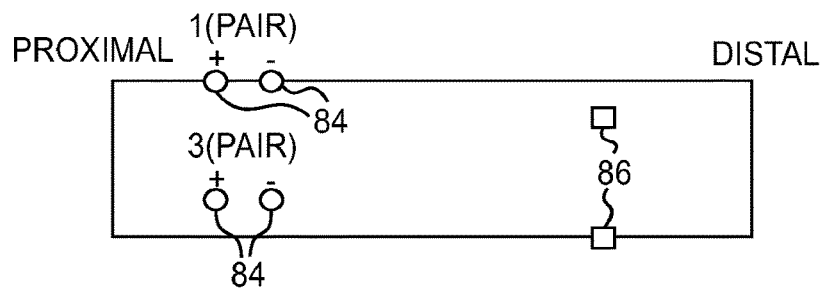
FIG. 5A
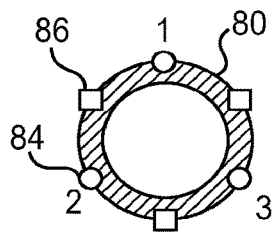 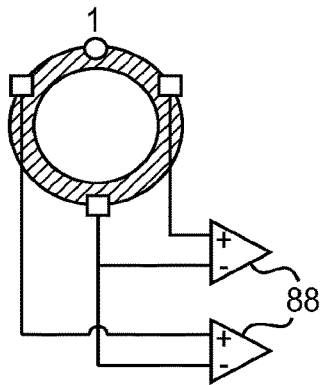 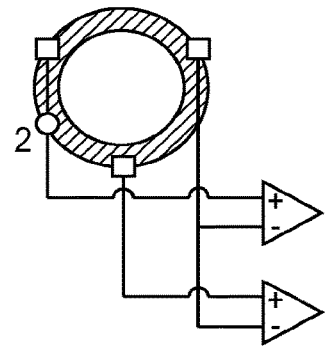
FIG. 5B  FIG. 5C  FIG. 5D
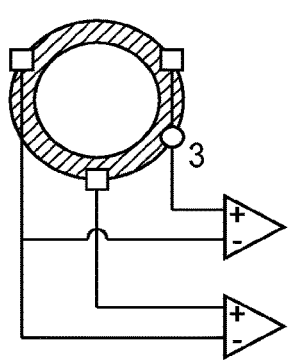 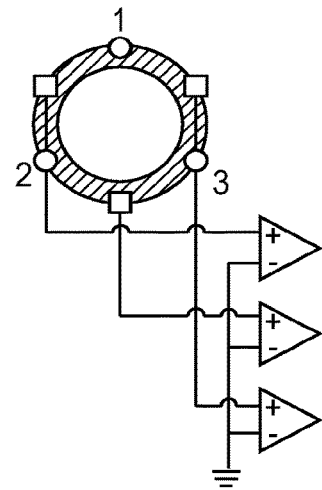
FIG. 5E  FIG. 5F

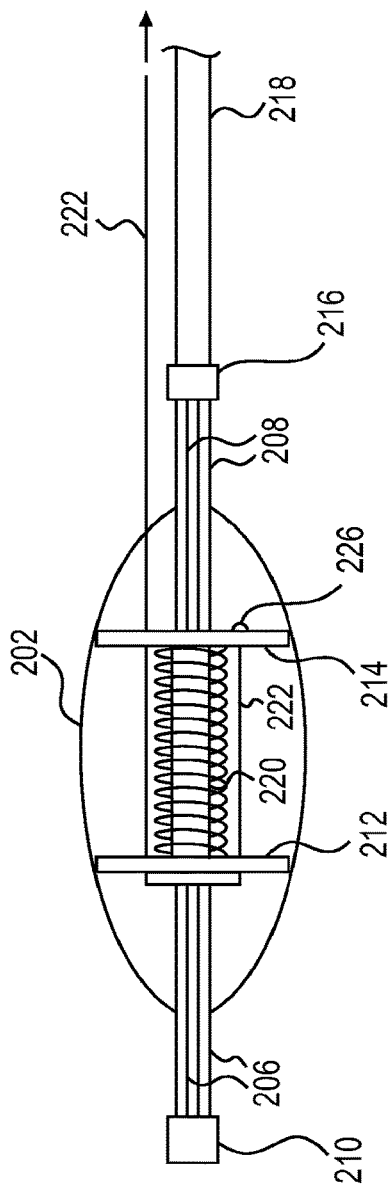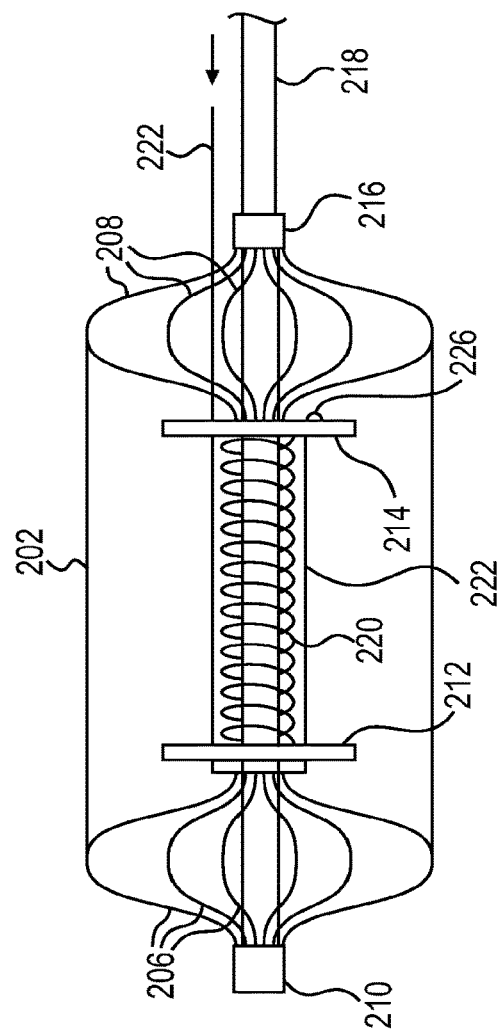

APPARATUS AND METHOD OF ASSESSING TRANSVASCULAR DENERVATION

RELATED APPLICATIONS

This application is a continuation of U.S. patent application Ser. No. 16/018,577, filed Jun. 26, 2018, which is a continuation of U.S. patent application Ser. No. 14/537,109, filed Nov. 10, 2014, which is a continuation of U.S. patent application Ser. No. 13/153,838, filed Jun. 6, 2011, issued as U.S. Pat. No. 8,909,316, which is a continuation-in-part of U.S. patent application Ser. No. 13/110,041, filed May 18, 2011, each of which are incorporated herein by reference in their entireties.

BACKGROUND OF THE INVENTION

The present invention relates generally to catheter devices, and more specifically to catheter devices for assessing transvascular denervation.

Renal denervation is a method whereby amplified sympathetic activities are suppressed to treat hypertension or other cardiovascular disorders and chronic renal diseases. The objective of renal denervation is to neutralize the effect of renal sympathetic system which is involved in arterial hypertension. The following describes some examples of renal denervation devices. U.S. Pat. No. 7,653,438 discloses renal neuromodulation using a pulsed electric field to effectuate electroporation or electrofusion. It describes percutaneous intravascular delivery of pulsed electric fields to achieve renal neuromodulation. U.S. Patent Application Publication No. 2010/0268307 discloses intravascularly induced neuromodulation using a pulsed electric field to effectuate irreversible electroporation or electrofusion, necrosis, and/or inducement of apoptosis, alteration of gene expression, changes in cytokine upregulation, etc., in target neural fibers. It mentions the use of the technique to modulate a neural fiber that contributes to renal function. International Patent Publication No. WO2008/092246 discloses transvascular nerve stimulation through the walls of blood vessels. It uses electrodes supported on an electrically insulating backing sheet and a structure for holding the backing sheet against the inner wall of the blood vessel.

Catheters are flexible, tubular devices that are widely used by physicians performing medical procedures to gain access into interior regions of the body. A catheter device can be used for ablating renal sympathetic nerves in therapeutic renal sympathetic denervation to achieve reductions of blood pressure in patients suffering from renal sympathetic hyperactivity associated with hypertension and its progression. See, e.g., Henry Krum et al., Catheter-Based Renal Sympathetic Denervation for Resistant Hypertension: A Multicentre Safety and Proof-of-Principle Cohort Study, published online Mar. 30, 2009 at www.thelancet.com.

Renal arteries, like all major blood vessels, are innervated by perivascular sympathetic nerves that traverse the length of the arteries. The perivascular nerves consist of a network of axons, terminals, and varicosities, which are distributed mostly in the medial-adventitial and adventitial layers of the arterial wall. The medial and adventitial layers of the renal artery consist mostly of vascular smooth muscle cells (VSMCs), while the intimal layer is made up of endothelial cells (ECs). A small percentage of the VSMCs in the adventitia of the renal artery have a direct coupling to the varicosities because of their proximity to each other. When the renal sympathetic nerve is stimulated and an action potential travels along the axon, all varicosities along the axon are depolarized and neurotransmitters are released into the junctions of directly-coupled VSMCs. This event causes the opening of specific ionic and second messenger molecule channels of the VSMCs and results in their depolarization.

The depolarization described above would normally be confined to the first layer of the VSMCs that are directly coupled to the varicosities because extracellular diffusion of neurotransmitters is characterized by a small space and time constant. Therefore in theory any recording of excitatory junction potentials (EJPs) should be done at the directly coupled VSMCs. However, numerous studies of vasomotion of arteries have led to the understanding that additional VSMCs are recruited in generating a syncytial response to neural stimulation. Thus gap junctions have been identified amongst VSMCs and ECs, and between VSMCs and ECs. These gap junctions form the conduit for intercellular communication and facilitate neurotransmitter diffusion over a larger space constant than can be accounted for by extracellular diffusion alone. Intercellular diffusion is dependent on gap junction permeability and decays as it crosses each junction. Recording of EJPs have been shown to take place within a few millimeters from perivascular nerves.

EJP recordings are commonly performed using intracellular techniques. The recording electrodes are typically made of glass micropipettes that impale a single cell to provide an isolated signal path to an amplifier. In other techniques, suction is applied to provide a high impedance seal between the glass micropipette and cell membrane without having to penetrate the cell. The high impedance seal isolates signal conduction between the cell membrane and the electrode from environmental noise. Extracellular recording of junction potentials are possible but more challenging because of the much smaller potential amplitude at the surface of the cell and the electronics requirements for noise reduction. Depending on the size of the recording electrode, extracellular recording may record from a single cell or an ensemble of cells. The latter is analogous to field potential recording from multi-neurons in the brain.

In certain animal arteries such as rat tail arteries and mesenteric arteries, recording of spontaneous EJPs (SEJPs) have been reported. These SEJPs occur asynchronously following normal sympathetic activities of the animal physiology. On average the recording of these asynchronous SEJPs will cancel out within a field potential recording technique, regardless of the fidelity of the recording electronics. On the other hand, when perivascular nerves are stimulated under external control, EJPs occur synchronously with the stimulus source, thus enabling evoked responses to be detected in the recording. Common techniques for electrical perivascular nerve stimulation include both nerve trunk stimulation and transmural (field) stimulation. Both techniques require direct electrode access to the adventitial area of the artery. With transmural stimulation, the stimulus strengths are designed to be supramaximal to activate the perivascular nerves without directly stimulating the VSMCs.

Transvascular technique of electrical stimulation of perivascular nerves is not as widely reported. One possible explanation is the stimulus strength required to activate the perivascular nerves will most likely also stimulate the VSMCs directly (this is because the electrical current density from the electrode attenuates as a function of distance and the VSMCs are closer to the stimulating electrodes than the perivascular nerves), thus making it difficult to analyze neurally evoked responses independently. Most electrical stimulus consists of square pulses and by using shorter pulse widths it may be possible to selectively activate the perivascular nerves only. However, a better method is to make use of the anisotropy of VSMCs and the finite space constants of EJPs to differentiate neurally evoked responses from field evoked responses, so that perivascular nerve integrity can be independently assessed. Thus in a preferred arrangement, the stimulating electrodes and recording electrodes should be separated by a distance greater than the EJP space constant in the longitudinal direction of the vessel. In this way, the recording electrodes will only record EJPs evoked by action potentials traveling distally along the axon, while excluding EJPs evoked in the vicinity of the stimulating electrodes.

BRIEF SUMMARY OF THE INVENTION

Prior denervation devices do not provide any means of predicting the long term outcome of the renal denervation therapies. Nor do they provide a marker to assess the completeness of the therapeutic procedure. In the case where denervation is carried out by delivering continuous RF energy through the vascular wall, the typical target procedural parameters are impedance, elapsed time, temperature or power, or a combination of all the above. The correlation of these parameters with the extent of denervation has never been shown, and may not be tenable given the heterogeneous nature of vascular innervation structures. There is therefore a need to provide a more direct technique of measuring residual neural activities following denervation in order to assess the completeness of such procedures.

Exemplary embodiments of the invention provide catheter devices for assessing transvascular denervation. The patency of the innervation of vessels can be assessed directly through electrophysiological techniques. Specifically, appropriately positioned sensors are deployed in direct contact with the vessel luminal wall to record evoked responses from external stimulus. Excitatory junctional potentials from the VSMCs can be recorded. Mechanical responses (vasoconstriction or vasodilation) associated with these neural events can also be monitored. By comparing the pre-treatment recording with post-treatment recording, a DeNervation Assessment index (DNAi) can be derived.

In accordance with an aspect of the present invention, a catheter apparatus for assessing denervation comprises: an elongated catheter body having a proximal end and a distal end, a longitudinal axis extending in a longitudinal direction between the distal end and the proximal end; a deployable structure coupled to the catheter body, the deployable structure being deployable outwardly from the longitudinal axis and contractible inwardly toward the longitudinal axis of the catheter body; one or more ablation elements disposed on the deployable structure to move outwardly and inwardly with the deployable structure, the one or more ablation elements being powered to apply ablation energy to a vessel of a patient; one or more stimulation elements spaced from each other and disposed on the deployable structure to move outwardly and inwardly with the deployable structure, the one or more stimulation elements being powered to supply nerve stimulating signals to the vessel; and one or more recording elements spaced from each other and from the one or more stimulation elements, the one or more recording elements being disposed on the deployable structure to move outwardly and inwardly with the deployable structure, the one or more recording elements configured to record response of the vessel to the nerve stimulating signals.

In some embodiments, the one or more stimulation elements are proximal relative to the one or more recording elements. A most distal ablation element of the one or more ablation elements is no more distal than at least one of the stimulation elements and a most proximal ablation element of the one or more ablation elements is no more proximal than at least one of the one or more recording elements. At least one of the ablation elements is also a stimulation element or a recording element. Some of the one or more recording elements are spaced from one of the one or more stimulation elements by one of a longitudinal spacing, a lateral spacing, or a combined longitudinal and lateral spacing. The one or more recording elements are configured to record one or more of evoked electrical responses or mechanical responses of the vessel in response to the nerve stimulating signals.

In specific embodiments, the deployable structure comprises a plurality of longitudinal spines, each of the spines having a proximal end connected to the catheter body and a distal end connected to the catheter body. Each spine includes an elbow having at least one discontinuity in stiffness at an intermediate position between the distal end and the proximal end thereof. The one or more ablation elements, the one or more stimulation elements, and the one or more recording elements are disposed on the spines. The deployable structure is contractible to a contracted arrangement to fit within a lumen of the elongated catheter body and is deployable to a deployed arrangement with the elbows of the spines bending outwardly relative to the proximal and distal ends of the spines, the elbows of the spines moving radially outwardly from the contracted arrangement to the deployed arrangement. The catheter apparatus further comprises a balloon disposed inside the deployable structure, the spines being disposed radially outwardly relative to the balloon, the balloon inflating to move the spines radially outwardly in the deployed arrangement and deflating in the contracted arrangement. One or more contact sensors are disposed on a surface of the balloon for measuring force or pressure.

In some embodiments, the deployable structure comprises a balloon made of an electrically insulative material, the balloon inflating to move radially outwardly relative to the catheter body in a deployed arrangement and deflating in an undeployed arrangement. The one or more ablation elements, one or more stimulation elements, and one or more recording elements are disposed on a surface of the balloon. An intraluminal pressure sensor is to be introduced and deployed inside the balloon for pressure monitoring.

In specific embodiments, the deployable structure comprises a deployable sleeve made of an electrically insulative material and a hollow tubing disposed inside the deployable sleeve. The hollow tubing includes a plurality of holes for fluid to pass therethrough to push the deployable sleeve radially outwardly relative to the catheter body in a deployed arrangement. The one or more ablation elements, the one or more stimulation elements, and the one or more recording elements are disposed on a surface of the deployable sleeve. The catheter apparatus further comprises a plurality of draw strings extending from inside the hollow tubing through the holes to the deployable sleeve to draw the deployable sleeve radially inwardly relative to the catheter body in an undeployed arrangement. The deployable structure is contractible to a contracted arrangement and is deployable to a deployed arrangement. The deployable structure includes an anti-occlusion feature to permit fluid flow in the vessel between a proximal end and a distal end of the deployable structure in the deployed arrangement.

In accordance with another aspect of the invention, a catheter apparatus for assessing denervation comprises: an elongated catheter body having a proximal end and a distal end, a longitudinal axis extending in a longitudinal direction between the distal end and the proximal end; a structure coupled to the catheter body; one or more ablation elements disposed on the structure and being powered to apply ablation energy to a vessel of a patient; one or more stimulation elements spaced from each other and disposed on the structure, the one or more stimulation elements being powered to supply nerve stimulating signals to the vessel; one or more recording elements spaced from each other and from the one or more stimulation elements, the one or more recording elements being disposed on the structure and configured to record response of the vessel to the nerve stimulating signals; and a mechanism to deploy the structure outwardly from the longitudinal axis of the catheter body to move the ablation elements, the one or more stimulation elements, and the one or more recording elements outwardly to a deployed arrangement, and to contract the structure inwardly toward the longitudinal axis of the catheter body to move the ablation elements, the one or more stimulation elements, and the one or more recording elements inwardly to a contracted arrangement.

In accordance with another aspect of this invention, a method of assessing denervation comprises: introducing intravascularly a catheter to a vessel of a patient, the catheter including one or more recording elements; performing a baseline recording of responses by supplying nerve stimulation to the vessel and recording responses of the vessel to the nerve stimulation; denervating at least some tissue proximate the vessel after performing the baseline recording; performing a post-denervation recording of responses, after the denervating, by supplying nerve stimulation to the vessel and recording responses of the vessel to the nerve stimulation; and assessing denervation of the vessel based on a comparison of the responses of the baseline recording and the responses of the post-denervation recording.

In some embodiments, the catheter is not repositioned during performing the baseline recording, denervating, and performing the post-denervation recording. The nerve stimulation comprises one of electrical stimulation or pharmacological stimulation. The responses include one or more of electrical response or mechanical response. Assessing denervation of the vessel comprises: computing a baseline parameter from the responses of the baseline recording; computing a post-denervation parameter from the responses of the post-denervation recording; and computing a degree of denervation as a ratio of the post-denervation parameter and the baseline parameter. Denervation is achieved when the computed ratio falls within a preset range. The baseline parameter is computed based on a baseline maximum signal amplitude of one or more evoked responses generated in response to the nerve stimulation and recorded by the one or more recording elements before the denervating. The post-denervation is computed based on a post-denervation maximum signal amplitude of one or more evoked responses generated in response to the same nerve stimulation and recorded by the one or more recording elements after the denervating. The one or more evoked responses include one or more of evoked electrical response or evoked mechanical response.

In specific embodiments, the baseline parameter is computed based on a baseline area under a plot of one or more evoked responses generated in response to the nerve stimulation and recorded by the one or more recording elements before the denervating. The post-denervation is computed based on a post-denervation area under a plot of one or more evoked responses generated in response to the same nerve stimulation and recorded by the one or more recording elements after the denervating. The method further comprises, if denervation of the vessel is not achieved, repeating the steps of denervating, performing a post-denervation recording of responses, and assessing denervation of the vessel until denervation of the vessel is achieved. The repeating until denervation of the vessel is achieved is performed in real time. The catheter is not repositioned during the repeating. Repeating the steps of denervating, performing a post-denervation recording of responses, and assessing denervation of the vessel comprises adjusting a level of denervation for denervating at least some tissue proximate the vessel based on result of assessing denervation of the vessel. The repeating including the adjusting until denervation of the vessel is achieved is performed in real time.

In some embodiments, recording responses of the vessel to the nerve stimulation comprises recording one or more of evoked electrical responses or mechanical responses of the vessel in response to the nerve stimulation. The vessel is denervated using one or more ablation elements disposed on the catheter. The catheter is not repositioned during performing the baseline recording, denervating, and performing the post-denervation recording. The catheter includes one or more stimulation elements to supply nerve stimulating signals as the nerve stimulation.

In specific embodiments, the method further comprises deploying a deployable structure to enhance contact between the one or more stimulation elements and the vessel and between the one or more recording elements and the vessel. The method further comprises providing electrical insulation between the one or more stimulation elements and the one or more recording elements to facilitate signal conduction between the one or more stimulation elements and tissue proximate the vessel and to facilitate signal conduction between the one or more recording elements and tissue proximate the vessel. The method further comprises deploying a deployable structure to enhance contact between the one or more recording elements and the vessel.

These and other features and advantages of the present invention will become apparent to those of ordinary skill in the art in view of the following detailed description of the specific embodiments.

BRIEF DESCRIPTION OF THE DRAWINGS

FIGS. 5A-5F show different configurations of the stimulating and recording electrodes of the deployable sleeve of FIG. 4.

FIGS. 8A and 8B are elevational views of a catheter device with a deployable sleeve having an anti-occlusion feature according to another embodiment of the present invention.

DETAILED DESCRIPTION OF THE INVENTION

Figure 1:
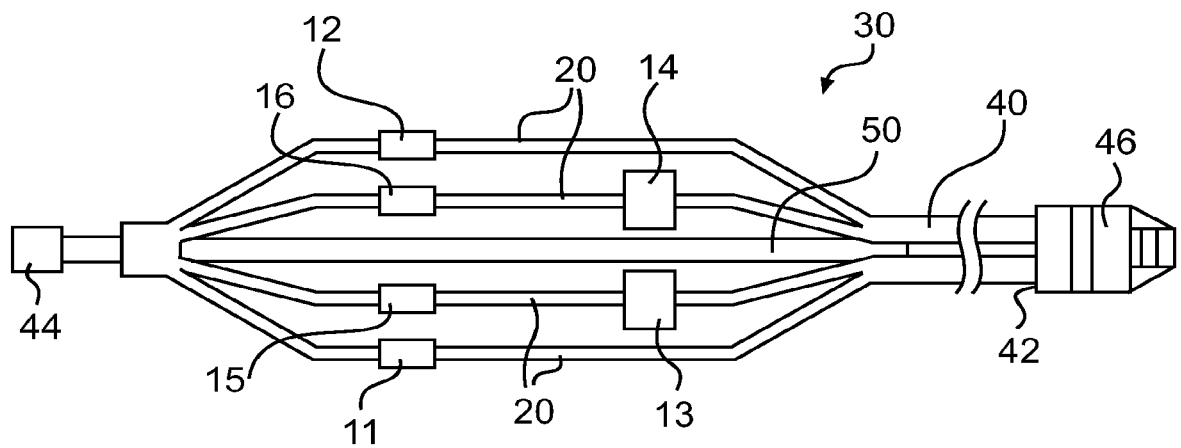
FIG. 1 is an elevational view of a catheter device with a deployable basket for assessing transvascular denervation according to an embodiment of the present invention.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment", "this embodiment", or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide apparatuses and methods for assessing transvascular denervation.

FIG. 1 is an elevational view of a catheter device with a deployable basket for assessing transvascular denervation according to an embodiment of the present invention. The device integrates neural assessment elements with denervation elements for renal denervation or the like. In the specific embodiment shown, the denervation elements are configured as ablation electrodes. In other embodiments, the ablation/denervation element may employ other mechanisms or other types of energy (e.g., laser, high intensity focused ultrasound (HIFU), cryoablation, mechanical) to sever or interrupt conduction of the nerve fibers. FIG. 1 shows ablation electrodes 11, 12, 13, 14 and additional electrodes 15, 16 which are disposed on spines 20 in a deployable structure in a basket configuration 30 which is coupled to a catheter body 40. The catheter body 40 has a proximal end 42, a distal end 44, and a longitudinal axis extending in a longitudinal direction between the distal end 44 and the proximal end 42. An external catheter handle 46 is provided at the proximal end. The spines 20 are electrically nonconductive.

In this embodiment, the deployable basket 30 is coupled to the distal portion of the catheter body 40, and is deployable or expandable outwardly from the longitudinal axis and contractible inwardly toward the longitudinal axis of the catheter body 40. The basket 30 has a plurality of longitudinal spines 20 having distal ends and proximal ends that are attached to the catheter body 40. Each spine 20 includes an elbow having at least one discontinuity in stiffness at an intermediate position between the distal end and the proximal end thereof to allow the spine to expand/deploy and collapse/contract. Different mechanisms can be used to cause the expansion and collapse of the spines 20. In FIG. 1, a pull wire 50 extending along the longitudinal axis of the catheter body 40 is used to pull the distal end of the basket 30 in the proximal direction to deploy the basket 30. The basket 30 is in a deployed configuration in FIG. 1. To return the basket 30 to a contracted/undeployed configuration with the spines 20 extending generally longitudinally in the longitudinal direction, the spines 20 can be resiliently biased toward the contracted configuration and the pulling force on the pull wire 50 can be released to allow the basket 30 to contract. Alternatively, the pull wire 50 may be configured to apply a push force to push the distal end of the basket 30 in the distal direction to contract the basket 30. In a specific embodiment, the basket 30 is contractible to a contracted arrangement to fit within a lumen of the elongated catheter body 40 and is deployable to a deployed arrangement with the elbows of the spines bending outwardly relative to the proximal and distal ends of the spines 20, the elbows of the spines moving radially outwardly from the contracted arrangement to the deployed arrangement. An example of a similar deployable basket is found in US 2010/0076426 entitled Basket Catheter Having Multiple Electrodes, which is incorporated herein by reference in its entirety.

The pull wire 50 extends through a lumen of the catheter body 40. The lumen can also accommodate lines for supplying power to ablation electrodes, signals lines to stimulation electrodes and recording electrodes, fluid lines, and the like.

The electrodes 11, 12, 13, 14, 15, 16 are disposed on the deployable basket 30 to move outwardly and inwardly with the basket 30. The ablation electrodes 11, 12, 13, 14 are powered to apply ablation energy to a vessel of a patient such as a renal artery. Any of the ablation electrodes can also be stimulation or recording electrodes. Stimulation electrodes are powered to supply nerve stimulating signals to the vessel. The nerve stimulating signals are typically about 1 Hz to about 16 Hz and are designed to cause nerve excitation and evoke neurotransmitter release from perivascular varicosities. The stimulation thresholds will likely be much smaller than those for neuromodulation as taught in the art, since the intent is not to irreversibly electroporate the nerves. Recording electrodes are configured to record response of the vessel to the nerve stimulating signals. In some preferred embodiments, the recording electrodes are configured to record one or more of evoked electrical responses or mechanical responses of the vessel in response to the nerve stimulating signals. The stimulation electrodes are spaced from each other, the recording electrodes are spaced from each other, and the stimulation electrodes are spaced from the recording electrodes. As seen in FIG. 1, the spacing between the electrodes can be longitudinal, lateral/circumferential, or a combination of the two. Several stimulation and recording configurations are possible in FIG. 1. A first example includes stimulation electrodes 13, 15 and recording electrodes 14, 16 and 11, 12. A second example includes stimulation electrodes 14, 16 and recording electrodes 13, 15, and 11, 12. A third example includes stimulation electrodes 11, 12 and recording electrodes 13, 15 and 14, 16. In some preferred embodiments, at least some of the stimulation electrodes are proximal relative to at least some of the recording electrodes. The stimulation electrodes 14, 16 are separated from the recording electrodes 11, 12, 13, 15 by at least a minimum distance, which is preferably approximately equal to the space constant of excitatory junction potentials (EJPs).

Nerve stimulation is preferably applied along the long axis of the vessel or artery since the nerve cells are aligned in that direction. To detect evoked responses, however, we are interested in the VSMCs which are aligned transverse to the nerves and hence the recording bipolar electrodes will preferably be oriented in the transverse direction accordingly. More particularly, the apparatus is set up to record from different configurations and orientations of electrodes simultaneously in order to maximize the likelihood of detection.

In FIG. 1, ablation is performed with two distal electrodes (11, 12) and two proximal electrodes (13, 14). Neural assessment is performed with a combination of the four ablation electrodes (11, 12, 13, 14) which also serve as stimulation or recording electrodes and two additional sensor electrodes (15, 16). In neural assessment, stimulating electrodes are typically parallel to the long axis of the vessel, while recording electrodes are made up of both transverse pairs and parallel pairs to the long axis of the vessel. Stimulation and recording typically involve separate sets of electrodes, but can be configured for simultaneous stimulation and recording with appropriate electronics circuits. Stimulation and recording can be performed using bipolar electrodes as shown in FIG. 1. Alternatively, monopolar and multipolar techniques can be used. For monopolar stimulation or recording, only one active electrode is required and an indifferent electrode is provided on the patient's tissue. Ablation is typically performed monopolarly, but bipolar or multipolar ablations are also possible with a different electrode arrangement. In some preferred embodiments, the most distal ablation electrode (11 or 12) is no more distal than at least one of the stimulation electrodes and the most proximal ablation electrode (13 or 14) is no more proximal than at least one of the recording electrodes.

Figure 2:
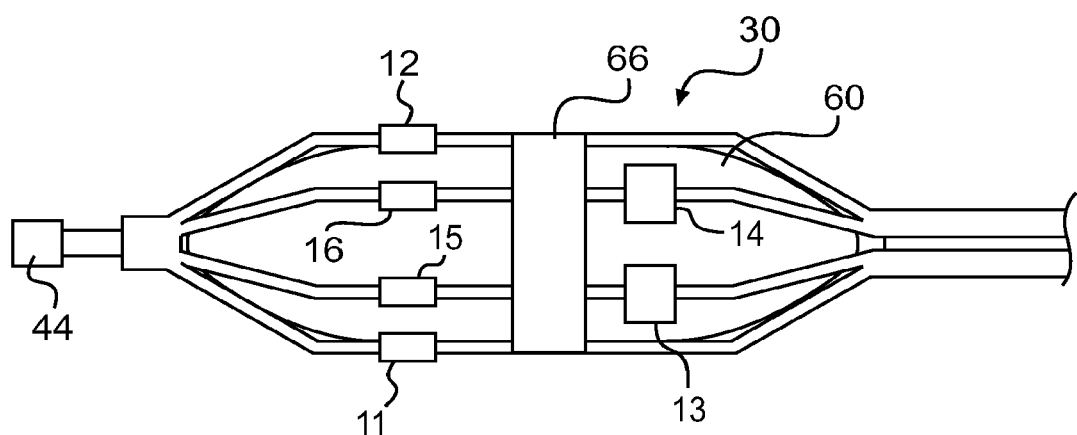
FIG. 2 is an elevational view of a catheter device with a balloon-augmented deployable basket according to another embodiment of the present invention.

FIG. 2 is an elevational view of a catheter device with a balloon-augmented deployable basket according to another embodiment of the present invention. This embodiment is similar to that of FIG. 1 with the addition of an elongated balloon 60 inside the basket 30 to replace the pull-wire expansion mechanism 50. It inflates to expand the basket 30 outwardly in the deployed arrangement and deflates in the contracted/undeployed arrangement. This embodiment enhances tissue and electrode contact for both ablation and neural assessment. The balloon-augmented catheter is first deflated and positioned at the target renal artery site. Then the balloon 60 is inflated with saline or the like to a preset volume for neural assessment and ablation. The balloon 60 is preferably made of an electrically insulative material, which facilitates signal conduction between the stimulation electrodes and the tissue proximate the vessel and to facilitate signal conduction between the recording electrodes and the tissue proximate the vessel. The electrically insulative balloon 60 preferably permits the least resistive path for signal conduction between the stimulation electrodes and the tissue and between the recording electrodes and the tissue.

The contact force or pressure between the vessel wall and the balloon 60 is transmitted to the fluid inside the balloon 60 and measured proximally at the external catheter handle 46 via suitable instruments; alternatively, additional electromechanical contact force/pressure sensors 66 can be incorporated on the surface of the balloon 60 to record changes in the luminal wall force/pressure. FIG. 2 shows a circumferential band of contact force/pressure sensors 66, but other sensor configurations are possible. The method of mechanical sensing here is advantageous since it is less susceptible to interference with the source of stimulus which is of a different modality (electrical). The balloon 60 may be made of a variety of materials including, for example, polyurethane or nylon.

Figure 3:
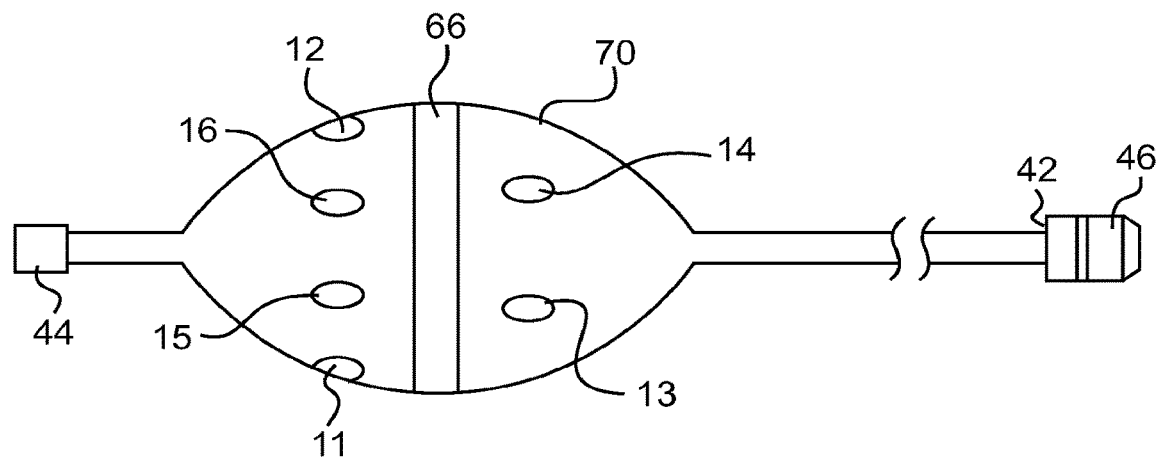
FIG. 3 is an elevational view of a catheter device with a deployable balloon according to another embodiment of the present invention.

FIG. 3 is an elevational view of a catheter device with a deployable balloon according to another embodiment of the present invention. This embodiment is similar to that of FIG. 2 but eliminates the basket and employs a balloon 70 with integrated electrodes. The electrodes may be embedded with the balloon material or printed on through a thin film deposition process. For simplicity, FIG. 3 shows a similar set of electrodes 11, 12, 13, 14, 15, 16 and force/pressure sensors 66 as those in FIGS. 1 and 2. The balloon 70 may have some or all of the same features and characteristics as the balloon 60 of FIG. 2 as described above.

Figure 4:
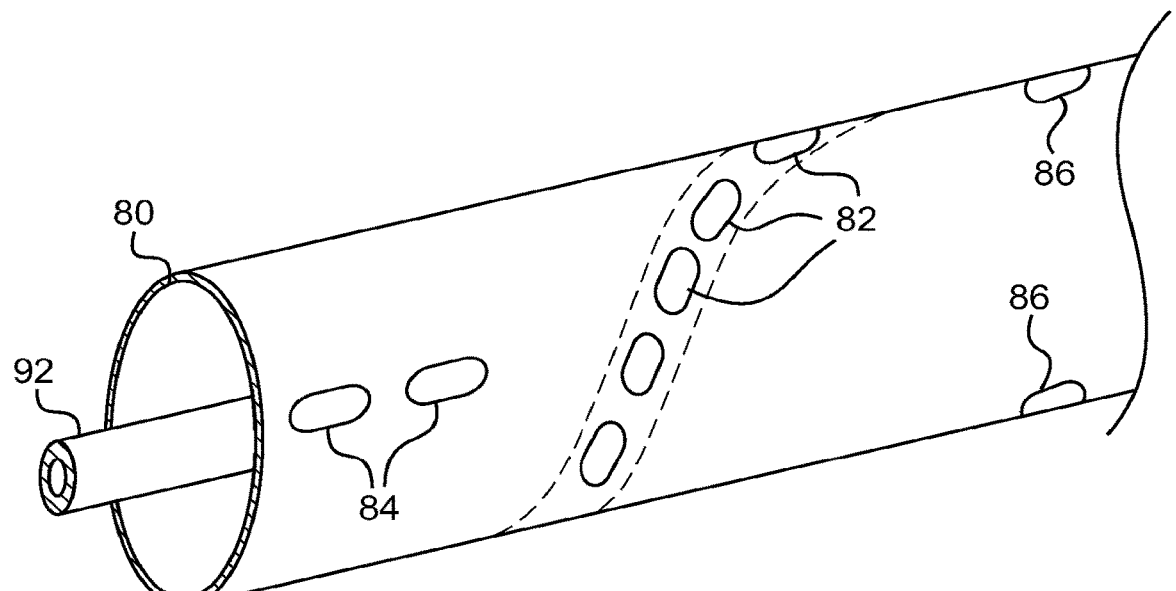
FIG. 4 is a perspective view of a catheter device with a deployable sleeve according to another embodiment of the present invention.

FIG. 4 is a perspective view of a catheter device with a deployable sleeve according to another embodiment of the present invention. This embodiment makes use of a deployable sleeve 80 instead of a balloon to insulate the electrodes from the blood in the vessel. The sleeve 80 is preferably made of an electrically insulating material. Various arrangements of electrodes for ablation and assessing denervation can be utilized. As an example, a spiral strip (not shown) of ablation electrode can be attached to the outside of the sleeve 80 and along the long axis of the sleeve 80. Alternatively, the single strip may be divided into multiple ablation electrodes 82 connected in series to form a spiral arrangement along the outside of the sleeve 80. This is the arrangement, for example, when monopolar ablation is desired and output power is divided equally across all ablation electrodes. Alternatively, ablation can be performed preferentially by bipolar means. In this case, pairs of electrodes can be grouped to create bipolar lesions that are larger and more contiguous than if monopolar lesions were created. A plurality of bipolar sets of stimulation electrodes 84 (FIGS. 4 and 5A-5F show three pairs each being parallel to the long axis of the sleeve 80) and a plurality of recording electrodes 86 (FIGS. 4 and 5A-5F show three) are attached to each side of the ablation electrodes 82 respectively. The three pairs of stimulation electrodes 84 are distributed circumferentially to provide circumferential coverage of nerves. Each pair of stimulating electrodes 84 can be energized to evoke responses to be recorded with the recording electrodes 86.

FIGS. 5A-5F show different configurations of the stimulating and recording electrodes of the deployable sleeve 80 of FIG. 4. The elevational view of FIG. 5A and the end view of FIG. 5B (from proximal end) illustrate the arrangement of the three pairs of stimulating electrodes 84 and three recording electrodes 86. The ablation electrodes are omitted for simplicity. FIG. 5C shows a recording configuration with the first pair of stimulation electrodes 84 active (other pairs are omitted for simplicity). The active stimulation electrodes 84 and recording electrodes 86 are connected to recording amplifiers 88. FIG. 5D shows a recording configuration with the second pair of stimulation electrodes 84 active (other pairs are omitted for simplicity). FIG. 5E shows a recording configuration with the third pair of stimulation electrodes 84 active (other pairs are omitted for simplicity). FIG. 5F shows a recording configuration with all three pairs of stimulation electrodes 84 active. A total of three contiguous stimulation-recording periods can be performed, for both baseline and post-denervation assessments. Alternatively, all three stimulating electrode pairs 86 are energized simultaneously, while evoked responses are recorded between each recording electrode 86 and an indifferent electrode or electronic ground.

Lead wires for all the electrodes as well as thermocouple wires are embedded within the sleeve substrate. During ablation the ablation electrode circuit is closed, while the neural assessment electrode circuit is open. Following ablation, the opposite is true for neural assessment, i.e., the ablation electrode circuit is open, and the neural assessment electrode circuit is closed. Additional electromechanical sensors for force/pressure sensing and the like can likewise be incorporated as the sensors 66 on the balloons 60, 70 of FIGS. 2 and 3. The sleeve 80 may be made of a variety of materials including, for example, polyurethane or nylon.

Figure 6:
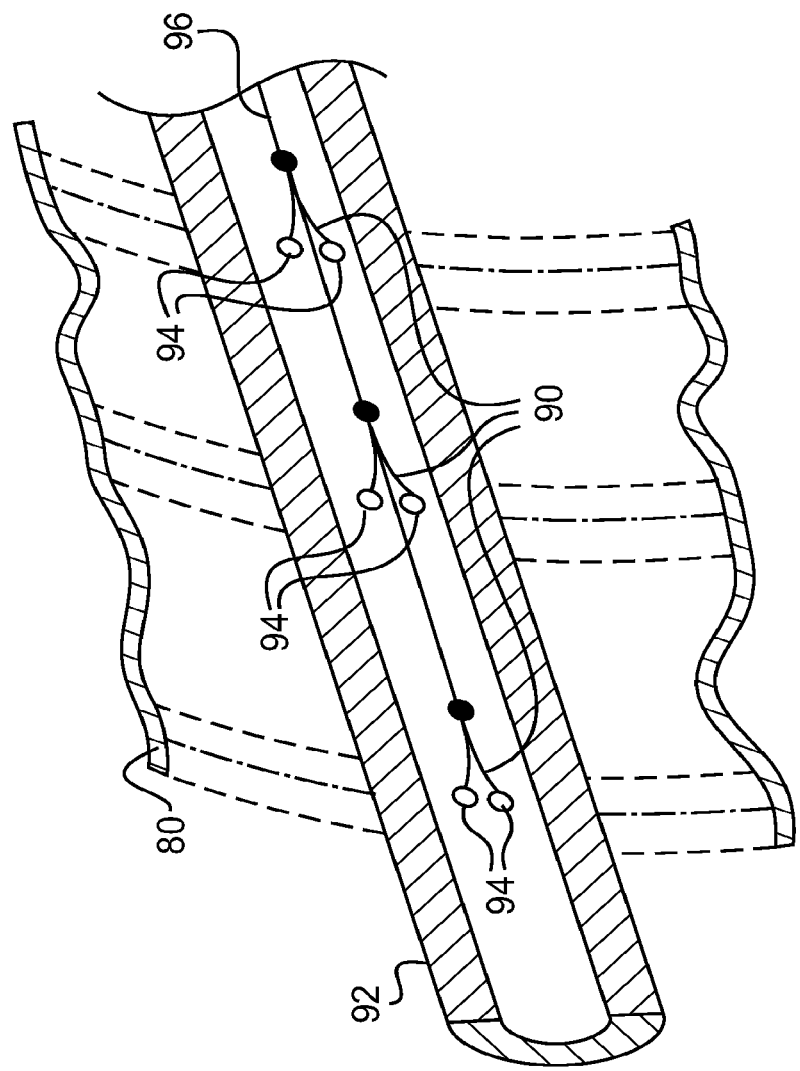
FIG. 6 is a perspective view of a partially cut-out section of the catheter device of FIG. 4.

FIG. 6 is a perspective view of a partially cut-out section of the catheter device of FIG. 4. The sleeve 80 is moved between a deployed arrangement and a contracted/undeployed arrangement using any suitable mechanism. The sleeve 80 is open and non-occlusive, except for the mechanism of deploying and contracting. In the example seen in FIG. 6, the sleeve 80 is contracted using three sets of draw strings 90 located near the distal and proximal ends as well as midpoint of the sleeve 80. The draw strings 90 are drawn into a hollow tubing 92, which is capped at the distal end, through the holes 94 per draw string 90. All three draw strings 90 are joined together at a proximal distance by a pull wire 96 that is controlled at the proximal catheter handle 46. To release the draw strings 90, the handle 46 will first advance the pull wire 96 to relax the draw strings 90, and then a bolus of saline or the like is injected through the tubing 92 creating an outward pressure at the draw string holes 94 (and optionally additional holes) and forces the sleeve 80 to expand towards the vascular wall, thus insulating the electrodes from the vessel. To move the sleeve 80 to the contracted arrangement, the pull wire 96 is retracted at the handle 46 to pull the draw strings 90 to draw the sleeve 80 radially inwardly. The non-occlusive sleeve 80 is deployed by exerting a positive differential pressure by the injected fluid against the blood in the vessel, and once deployed, is kept in place (i.e., in contact with vessel wall) by the blood pressure. In the reverse action of contracting, the draw strings 90 are retracted into the hollow tubing 92 by the pull wire 96, having overcome the positive blood pressure exerted against the sleeve 80.

Figure 7:
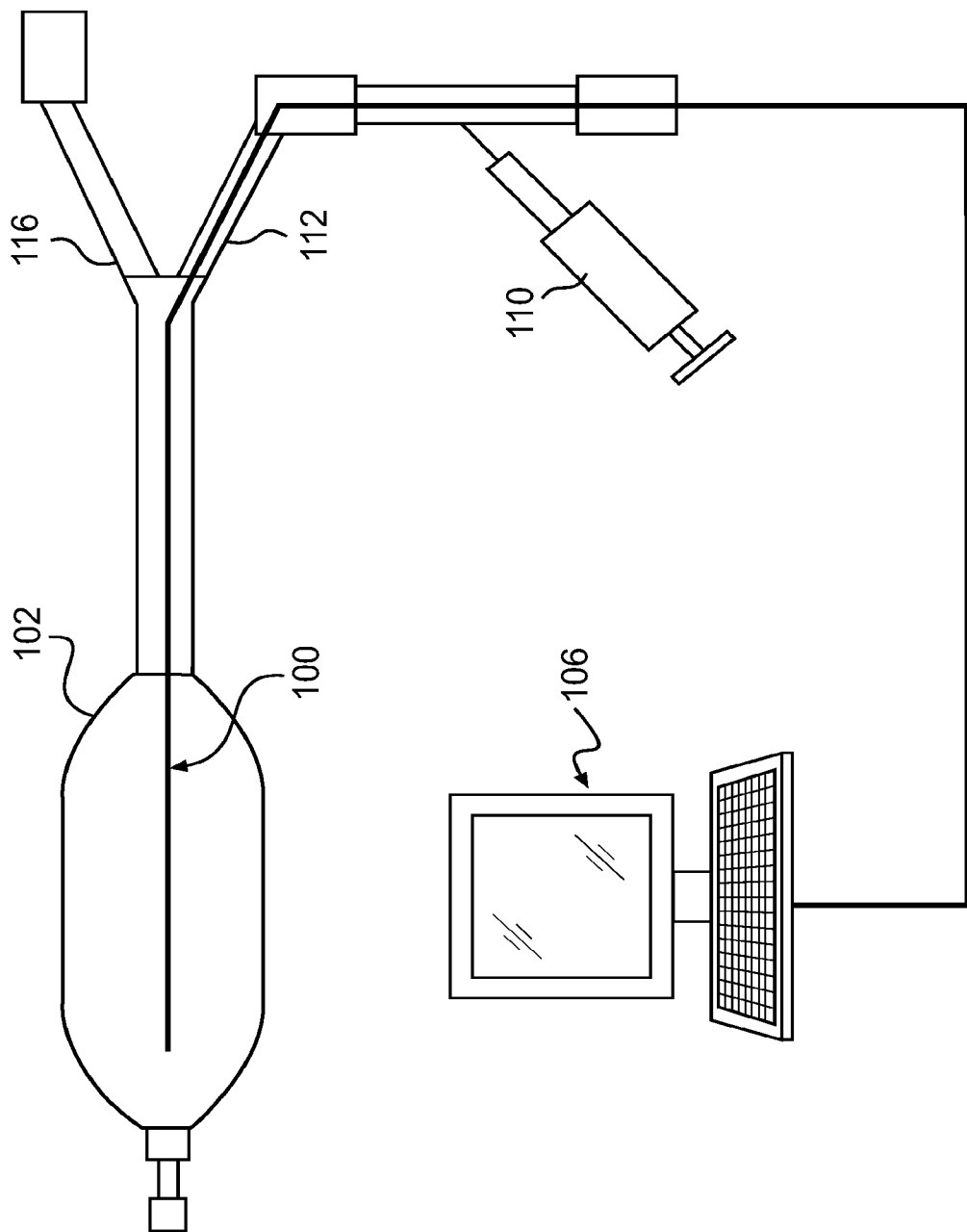
FIG. 7 is a schematic view illustrating an apparatus to provide an intraluminal pressure sensor for use with the catheter device.

FIG. 7 is a schematic view illustrating an apparatus to provide an intraluminal pressure sensor for use with the catheter device. In the embodiment shown, the intraluminal pressure sensor 100 is introduced proximally and deployed inside the balloon 102 (which may be balloon 60 of FIG. 2 or balloon 70 of FIG. 3) for pressure monitoring while maintaining the balloon 102 isovolumic. The apparatus of FIG. 7 includes an analyzer 106 coupled to the pressure sensor 100, a syringe 110 and a fluid port 112 for introducing a fluid into the balloon 102, and an electrical port 116 for supplying electrical energy to the catheter device. This provides an alternative or an additional mechanism for pressure sensing while maintaining the balloon 102 isovolumic.

Figure 8:
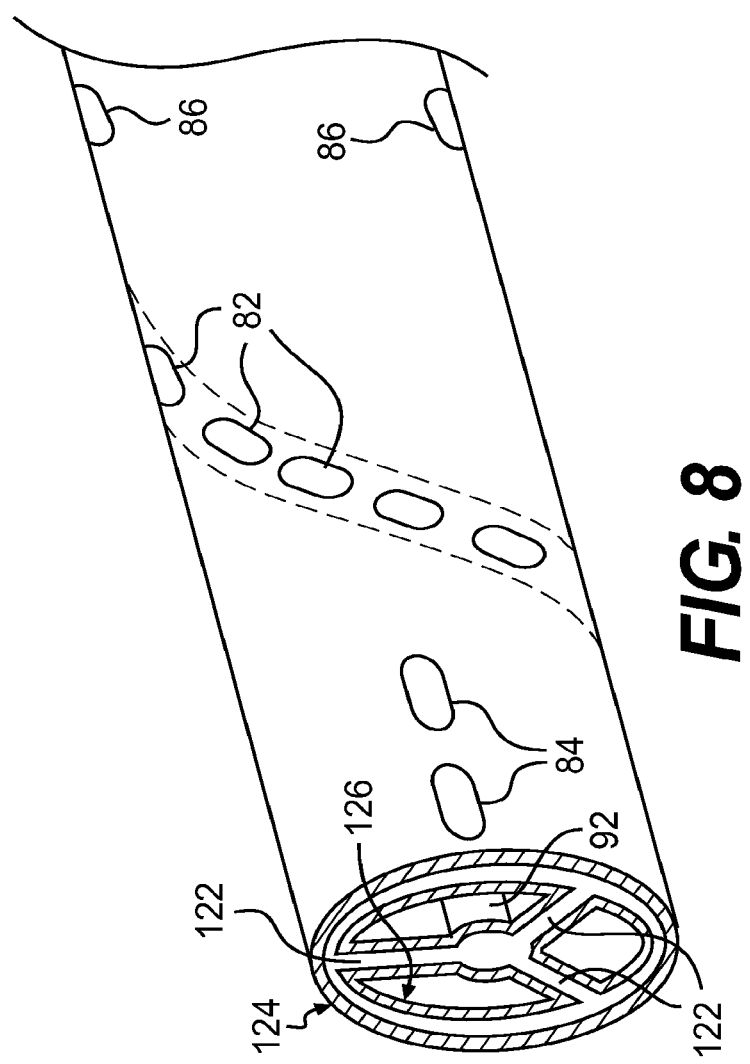
FIG. 8 is a perspective view of a catheter device with a deployable sleeve having an anti-occlusion feature according to another embodiment of the present invention.

FIG. 8 is a perspective view of a catheter device with a deployable sleeve having an anti-occlusion feature according to another embodiment of the present invention. This embodiment is similar to that of FIGS. 4 and 5 but the sleeve structure is modified to provide an anti-occlusion feature to permit blood/fluid flow in the vessel between the proximal end and the distal end of the deployable sleeve structure in the deployed arrangement. In FIG. 8, the sleeve 120 remains flexible and has electrodes similar to those in FIG. 4. A plurality of rib channels 122 are used to connect the lumen of the hollow tubing 92 to an enclosed interior of sleeve 120 between its outer shell 124 and inner shell 126. The interior of the sleeve 120 and the rib channels 122 are capped or closed at the proximal and distal ends. The inner shell 126 of the sleeve 120 is preferably noncompliant so that it does not stretch or expand beyond its preset expanded shape. The outer shell 124 of the sleeve 120 is preferably semi-compliant so that it can stretch under the pressure of the fluid supplied to the interior of the sleeve 120 to enhance contact between the electrodes and the vessel wall. The rib channels 122 span the length of the sleeve 120 and are preferably flexible but noncompliant. Open flow paths are provided between the rib channels 122 to permit fluid flow in the vessel between the proximal end and the distal end of the sleeve 120 in the deployed arrangement.

FIGS. 8A and 8B are elevational views of a catheter device with a deployable sleeve having an anti-occlusion feature according to another embodiment of the present invention. The sleeve 202 is undeployed in FIG. 8A and deployed in FIG. 8B. The sleeve 202 is connected or bonded to a set of distal spines 206 and a set of proximal spines 208. The distal spines 206 are connected between a distal termination end 210 and a distal retainer 212. The proximal spines 208 are connected between a proximal retainer 214 and a proximal termination end 216. The distal termination end 210 and proximal termination end 216 are both fixed to the catheter body 218, and are hence separated by a fixed distance. A resilient member such as a spring 220 is connected between the distal retainer 212 and the proximal retainer 214. A wire 222, which is a pull wire or a push-pull wire, is fixed at one end to a wire anchor 226 on the proximal retainer 214 and loops through holes in the proximal retainer 214 and the distal retainer 212 to the proximal portion of the catheter body 218. In FIG. 8A, the wire 222 is pulled to produce a pre-compressed spring 220. The distal spines 206 and proximal spines 208 as well as the sleeve 202 are in the collapsed/contracted/undeployed state. FIG. 8B shows the distal spines 206, proximal spines 208, and sleeve 202 in the expanded/deployed state. By releasing the tension on the wire 222, the spring 220 stretches, thereby pushing the distal retainer 212 and proximal retainer 214 apart. The distal retainer 212 moves toward the distal termination end 210 and the proximal retainer 214 moves toward the proximal termination end 216. This causes the distal spines 206 and the proximal spines 208 to expand laterally and deploy the sleeve 202 radially outwardly. The ends of the sleeve 202 are open in the deployed state of FIG. 8B, thereby allowing fluid flow in the vessel between the proximal end and the distal end of the sleeve 202 in the deployed arrangement without occlusion.

Other configurations of deployable structures and features can be used. For example, a deployable structure may be formed by a plurality of longitudinal strips that can be pulled in the longitudinal direction toward a straight configuration in the contracted/undeployed arrangement. When the pulling force is removed, the longitudinal strips expand radially outwardly into a spiral configuration in the deployed arrangement, under a resilient biasing force such as a memory shape material. Another example of a deployable structure is an S-shaped structure having one or more stimulating elements at the distal end thereof, one or more ablation elements on the first/distal hump of the S-shaped structure from the distal end thereof, and one or more recording elements on the second/proximal hump of the S-shaped structure from the distal end thereof. The S-shaped structure is preformed into the S-shape (e.g., using a shape memory material). It is stretched/deformed toward a straight configuration (e.g., using a stylet) in the contracted arrangement and is allowed to return to the S-shape in the deployed arrangement.

Figure 9:
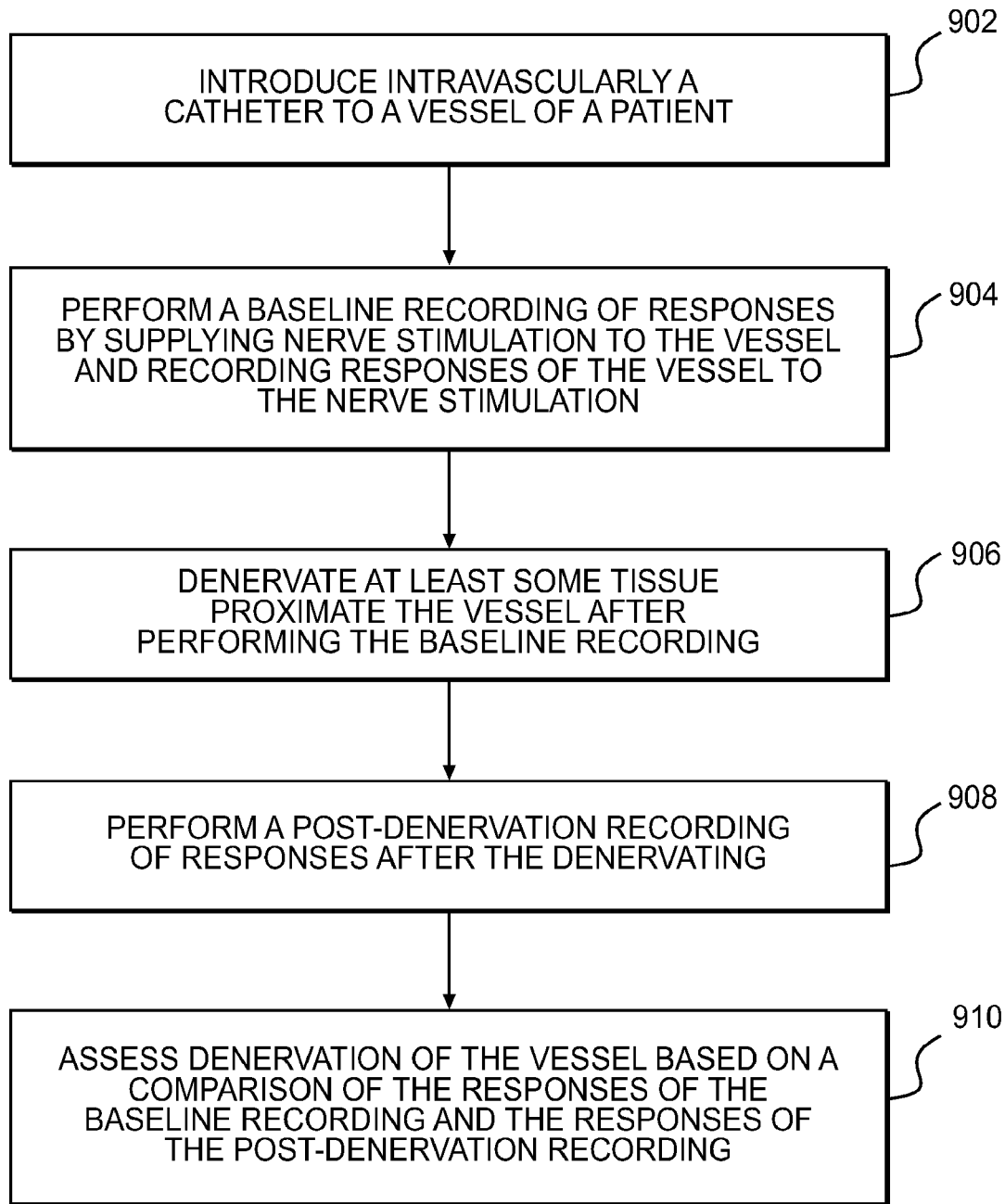
FIG. 9 shows an example of a flow diagram illustrating a method for assessing transvascular denervation.

FIG. 9 shows an example of a flow diagram illustrating a method for assessing transvascular denervation. To assess transvascular denervation using the apparatus described above, a user introduces intravascularly any of the above catheter devices to a target vessel of a patient and deploys it (step 902), and performs a baseline recording of responses by supplying nerve stimulating signals to the vessel with the stimulation electrodes and records responses of the vessel to the nerve stimulating signals using the recording electrodes (step 904). Next, the ablation electrodes are activated to ablate/denervate at least some tissue proximate the vessel (step 906). The user then performs a post-ablation recording of responses, after the denervating, by supplying nerve stimulating signals to the vessel with the stimulation electrodes and records responses of the vessel to the nerve stimulating signals using the recording electrodes (step 908). The user can assess denervation of the vessel based on a comparison of the responses of the baseline recording and the responses of the post-ablation recording (step 910). For stimulation and recording, it is preferable to deploy or expand a deployable structure (e.g., basket, balloon, sleeve, or the like) to enhance contact between the stimulation electrodes and the vessel wall and between the recording electrodes and the vessel wall. Ablation/denervation elements are preferably provided on the catheter device. As such, it is not necessary to reposition the catheter during the baseline recording, the ablation, and the post-ablation recording.

The responses include, for example, electrical response and/or mechanical response, which can be evoked excitatory junctional potentials or wall tension of the vessel in response to the nerve stimulating signals. In general, assessing denervation of the vessel includes computing a baseline parameter from the responses of the baseline recording, computing a post-ablation parameter from the responses of the post-ablation recording, and computing a degree of denervation as a ratio of the post-ablation parameter and the baseline parameter. The desired denervation is achieved when the computed ratio falls within a preset range. In one example, the baseline parameter is computed based on a baseline maximum signal amplitude of one or more evoked responses generated in response to stimulation of nerve stimulating signals by the stimulation elements and recorded by the recording elements before the ablating, and the post-ablation is computed based on a post-ablation maximum signal amplitude of one or more evoked responses generated in response to the same stimulation of nerve stimulating signals by the stimulation elements and recorded by the recording elements after the ablating. The evoked responses may include evoked electrical response and/or evoked mechanical response such as can be detected with a pressure sensor.

Figure 10:
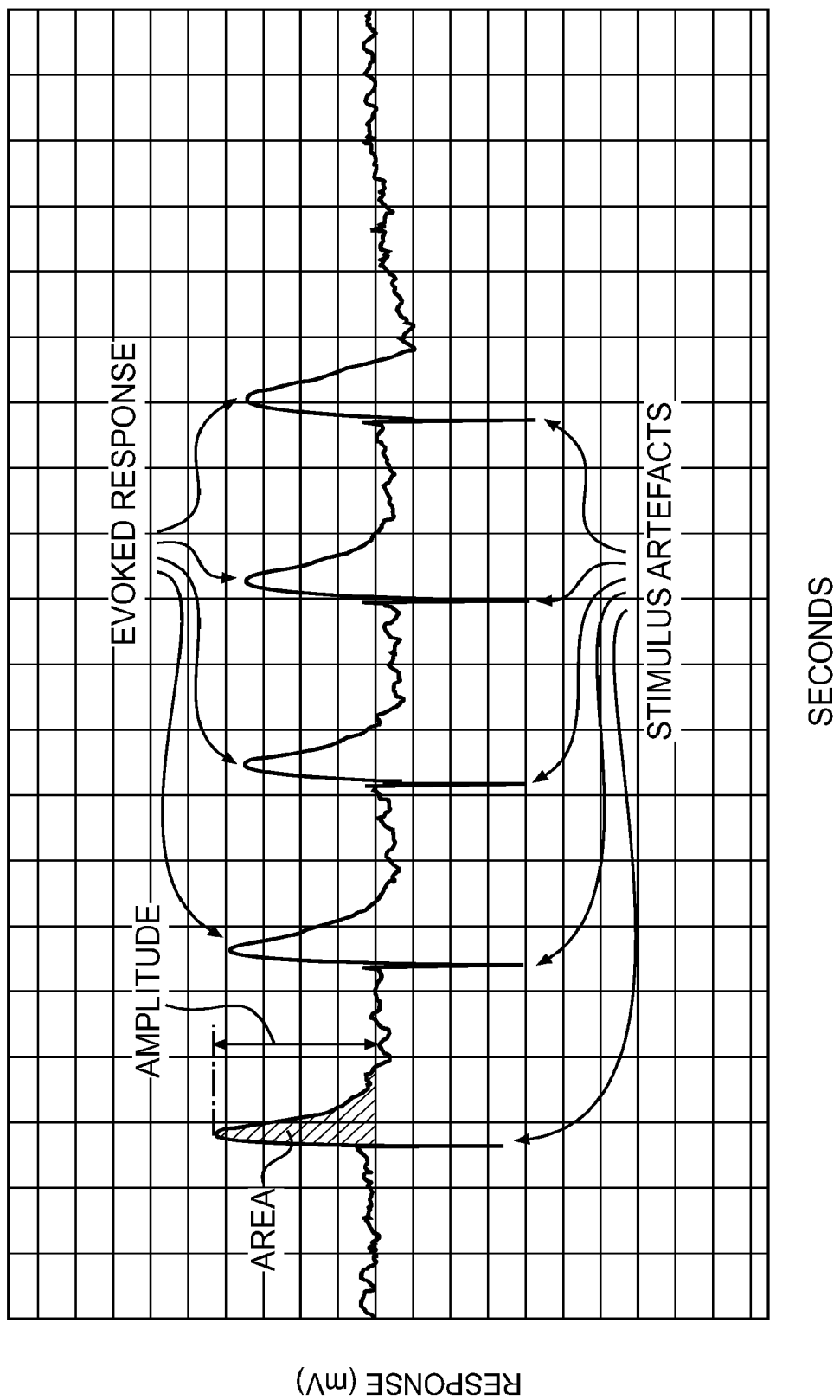
FIG. 10 shows an example of a plot of evoked responses and stimulus artifacts recorded by the recording elements.

In another example, the baseline parameter is computed based on a baseline area under a plot of one or more evoked responses generated in response to stimulation by the stimulation elements and recorded by the recording elements before the ablating, and the post-ablation is computed based on a post-ablation area under a plot of one or more evoked responses generated in response to the same stimulation by the stimulation elements and recorded by the recording elements after the ablating. FIG. 10 shows an example of a plot of evoked responses and stimulus artifacts recorded by the recording elements. The evoked responses each have an amplitude and an area. For multiple evoked responses, an average of the amplitudes or an average of the areas may be used to calculate the parameter.

If denervation of the vessel is not achieved, the user can repeat the steps of denervating (step 906), performing a post-ablation recording of responses (step 908), and assessing denervation of the vessel (step 910) until denervation of the vessel is achieved. The catheter need not be repositioned during the repeating. In some cases, repeating those steps include adjusting an energy level of ablation or a number of ablation elements for ablating tissue proximate the vessel based on the result of assessing denervation of the vessel. The repeating with or without the adjusting until denervation of the vessel is achieved is preferably performed in real time. The recording and assessing are preferably done in real time so that the assessment results can be provided as feedback to the user who can repeat the steps in real time, including adjusting the denervation in real time if necessary, to achieve the desired denervation for the patient undergoing the medical procedure in real time. If it is desired to adjust the position of the ablation or denervation elements the step of performing a baseline evoked response measurement should be repeated after the elements are repositioned and before the subsequent denervation step.

As an example, the baseline recording of evoked responses is performed to compute a parameters $A_i$ which can be derived from a number of variables such as the maximum signal amplitude or area under the first volley as mentioned above. The post-ablation assessment yields a second parameter $A_o$. The degree of denervation is computed as the $DNA_i$ given by $A_o/A_i$. The neural assessment method can be extended to provide closed loop control of denervation by interleaving ablation with neural assessment, for example, by incrementing the number of electrodes involved in ablation after each neural assessment until the $DNA_i$ is reduced below a certain threshold or falls within a preset range. This approach minimizes the need to move the catheter to different segments of the vessel for total coverage of denervation. Neural assessments can be done with bipolar or unipolar stimulation, but preferably bipolar. The bipolar stimulus can be either constant current or constant voltage, and is preferably a square wave with a pulse duration of about 0.1-1 millisecond, more preferably about 0.2-0.5 millisecond, and an amplitude of about 1-20 mA or 1-20 V, more preferably about 5-10 mA or 5-10 V. The stimulus is repeated typically at a rate of about 0.5-20 Hz for a total of about 5-30 seconds.

An alternative to electrical stimulation is pharmacological stimulation. Examples include the use of alpha-latrotoxin or ciguatoxin, which can be applied extraluminally (e.g., at 1 nM dose) to the renal artery. The drug can be delivered using a micro-infusion needle that penetrates the arterial wall to reach the perivascular axons. For instance, a balloon can be used to drive the needle into the arterial wall. The drug can temporarily activate or accelerate the release of neurotransmitters from perivascular varicosities and thus generate the evoked response for signal recording. The micro-infusion needle will replace the stimulation electrodes of the above embodiments while the recording electrodes are still used to record the response to the nerve stimulation produced by the drug.

The above-described method provides a direct and immediate assessment of the transvascular denervation procedure. It ensures optimal titration of energy to achieve denervation end point and provides a way to predict clinical outcome of denervation, preferably in real time.

In the description, numerous details are set forth for purposes of explanation in order to provide a thorough understanding of the present invention. However, it will be apparent to one skilled in the art that not all of these specific details are required in order to practice the present invention. It is also noted that the invention may be described as a process, which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged.

From the foregoing, it will be apparent that the invention provides methods, apparatuses and programs stored on computer readable media for ablation using an irrigated catheter device with multiple segmented ablation segments. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A method of evaluating the intraprocedural success of a renal denervation procedure on a subject, the method comprising:
   supplying, using a plurality of stimulating electrodes, first nerve-stimulating signals to multiple points about a circumference of a renal artery of the subject;
   recording, using a plurality of recording electrodes, a response of the renal artery to the first nerve-stimulating signals to determine a baseline physiological response of the subject;
   computing a first parameter from the baseline physiological response;
   performing a renal denervation procedure on the renal artery of the subject using an ablation catheter;
   supplying, using the plurality of stimulating electrodes, second nerve-stimulating signals to the multiple points about the circumference of the renal artery of the subject;
   recording, using the plurality of recording electrodes, a response of the renal artery to the second nerve-stimulating signals to determine a subsequent physiological response of the subject;
   computing a second parameter from the subsequent physiological response;
   computing a denervation index by dividing the second parameter by the first parameter;
   comparing the denervation index to a threshold value; and
   controlling operation of the ablation catheter based on the comparison of the denervation index to the threshold value.

2. The method of claim 1, wherein controlling operation of the ablation catheter comprises performing a subsequent renal denervation procedure using additional electrodes.

3. The method of claim 1 wherein the supplying of the first and second nerve-stimulating signals to the renal artery and the renal denervation are performed using the same ablation catheter.

4. The method of claim 3 wherein the ablation catheter includes at least four ablation electrodes and at least four electrical stimulation electrodes.

5. The method of claim 3, wherein the ablation catheter has an S-shaped structure.

6. The method of claim 5, wherein the S-shaped structure is deformable into a straight configuration.

7. The method of claim 5, wherein the S-shaped structure is made of a shape memory material.

8. The method of claim 3 wherein the ablation catheter is a balloon catheter.

9. The method of claim 3 wherein the ablation catheter comprises at least four ablation electrodes.

10. The method of claim 3 wherein the ablation catheter includes at least four splines.

11. The method of claim 1 wherein the first and second nerve-stimulation signals are supplied using sequential electrical stimulation.

12. The method of claim 1 wherein the first and second nerve-stimulation signals are supplied using simultaneous electrical stimulation.

13. The method of claim 1 wherein the first and second nerve-stimulation signals are supplied using monopolar electrical stimulation.

14. The method of claim 1 wherein the first and second nerve-stimulation signals are supplied using bipolar electrical stimulation.

15. The method of claim 1, wherein controlling operation of the ablation catheter comprises preventing the ablation catheter from performing a subsequent renal denervation procedure on the subject.

16. The method of claim 1, wherein computing a first parameter from the baseline physiological response comprising computing the first parameter based on i) a maximum signal amplitude of the baseline physiological response or ii) an area under a plot of the baseline physiological response.

* * * * *